United States Patent
Colin et al.

(10) Patent No.: US 9,738,864 B2
(45) Date of Patent: Aug. 22, 2017

(54) DETECTION DEVICE, SYSTEM AND METHOD MAKING IT POSSIBLE TO DETECT THE PRESENCE OF A MICRO-ORGANISM IN A SAMPLE OR INSIDE A CONTAINER

(71) Applicant: BIOMERIEUX, Marcy-l'Etoile (FR)

(72) Inventors: Bruno Colin, Marcy-l'Etoile (FR); Corinne De La Foata, Chicago, IL (US); Jacques Dachaud, Besancon (FR); Fabienne Made, Ecully (FR)

(73) Assignee: Biomerieux, Marcy-l'Etoile (FR)

( * ) Notice: Subject to any disclaimer, the term of this patent is extended or adjusted under 35 U.S.C. 154(b) by 0 days.

(21) Appl. No.: 14/896,817

(22) PCT Filed: Jun. 10, 2014

(86) PCT No.: PCT/EP2014/062024
§ 371 (c)(1),
(2) Date: Dec. 8, 2015

(87) PCT Pub. No.: WO2014/198718
PCT Pub. Date: Dec. 18, 2014

(65) Prior Publication Data
US 2016/0152940 A1 Jun. 2, 2016

(30) Foreign Application Priority Data
Jun. 11, 2013 (FR) ...................................... 13 55394

(51) Int. Cl.
*G01N 21/64* (2006.01)
*C12M 1/34* (2006.01)
(Continued)

(52) U.S. Cl.
CPC ............. *C12M 41/36* (2013.01); *C12M 41/06* (2013.01); *C12Q 1/04* (2013.01); *G01N 21/51* (2013.01);
(Continued)

(58) Field of Classification Search
CPC ......... C12M 41/36; C12M 41/06; C21Q 1/04; G01N 21/6428; G01N 2201/062; G01N 2201/12
See application file for complete search history.

(56) References Cited

U.S. PATENT DOCUMENTS 5,432,061 A * 7/1995 Berndt ................... C12M 41/36
356/318
5,483,080 A * 1/1996 Tam ....................... G01N 21/51
250/574
(Continued)

FOREIGN PATENT DOCUMENTS

EP 0635570 A2 1/1995
WO WO 94/07123 3/1994
WO WO 2012/016159 A2 2/2012

OTHER PUBLICATIONS

International Search Report and Written Opinion of corresponding International Patent Application No. PCT/EP2014/062024 mailed Jul. 24, 2014.

*Primary Examiner* — Sang Nguyen
(74) *Attorney, Agent, or Firm* — Pepper Hamilton LLP

(57) ABSTRACT

A device (10) for detecting the presence of at least one microorganism in the contents (101, 201) of a container (100, 200) comprising a wall with a translucent zone, said detection device (10) comprising:
a) at least one light source (11), such as a light-emitting diode (LED), capable of illuminating the contents of the container (100, 200) by emitting an excitation light beam through the translucent zone of the container (100, 200);

(Continued)

b) at least one detection means (12, 13, 14, 15), such as a photodiode, for detecting at least one reaction light beam emitted in response to the illumination of the contents (101, 201) of the container (100, 200);

said at least one light source (11) and said at least one detection means (12, 13, 14, 15) being equipped with at least one connection means (105, 205), to connect said at least one light source (11) and said at least one detection means (12, 13, 14, 15) to the wall of the container (100, 200), in the translucent zone, said at least one detection means (12, 13, 14, 15) being positioned at an angle of a set value in relation to the direction of the excitation light beam, to detect the reaction light beam.

20 Claims, 8 Drawing Sheets

(51) Int. Cl.

| | | |
|---|---|---|
| *C12Q 1/04* | (2006.01) | |
| *C12M 1/00* | (2006.01) | |
| *G01N 21/51* | (2006.01) | |
| *G01N 21/01* | (2006.01) | |
| *G01N 21/47* | (2006.01) | |

(52) U.S. Cl.
CPC ....... *G01N 21/645* (2013.01); *G01N 21/6428* (2013.01); *G01N 2021/0112* (2013.01); *G01N 2021/4709* (2013.01); *G01N 2021/4769* (2013.01); *G01N 2201/0221* (2013.01); *G01N 2201/062* (2013.01); *G01N 2201/12* (2013.01)

(56) References Cited

U.S. PATENT DOCUMENTS

| | | | | |
|---|---|---|---|---|
| 5,516,692 | A | * | 5/1996 | Berndt .................. B01F 9/002 422/63 |
| 5,705,384 | A | * | 1/1998 | Berndt .................. C12M 27/10 356/427 |
| 8,927,258 | B2 | * | 1/2015 | Galiano .............. G01N 35/028 435/286.2 |
| 2004/0070756 | A1 | * | 4/2004 | Rastopov ........... G01N 15/0211 356/338 |
| 2005/0254055 | A1 | | 11/2005 | Peng |
| 2006/0154327 | A1 | * | 7/2006 | Bachur, Jr. ............. C12M 41/34 435/34 |

* cited by examiner

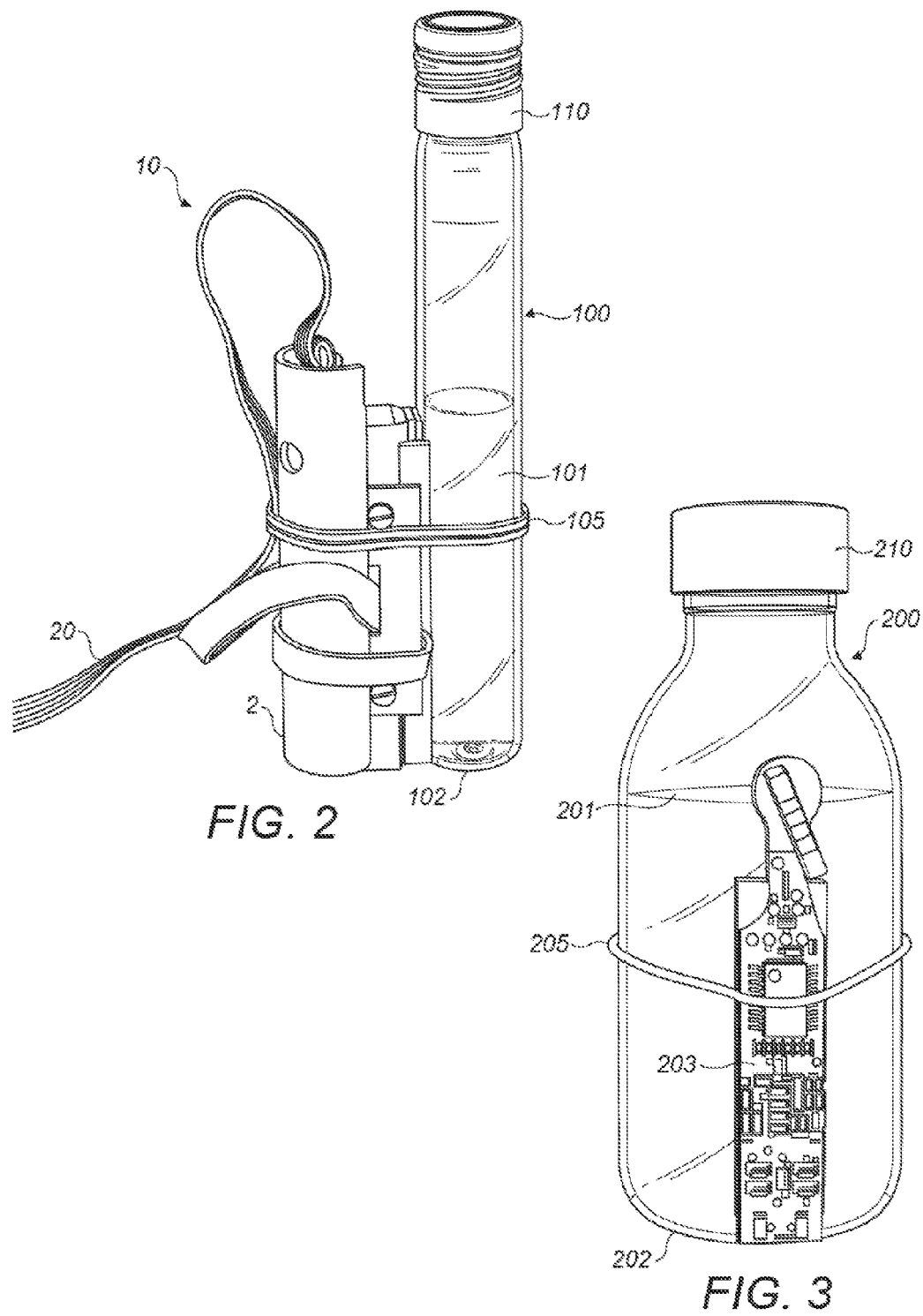

DETECTION DEVICE, SYSTEM AND METHOD MAKING IT POSSIBLE TO DETECT THE PRESENCE OF A MICRO-ORGANISM IN A SAMPLE OR INSIDE A CONTAINER

CLAIM OF PRIORITY

This application is a U.S. national stage filing under 35 U.S.C. §371 of International Application No. PCT/EP2014/062024 filed on Jun. 10, 2014 entitled "DETECTION SYSTEM, SYSTEM AND METHOD MAKING IT POSSIBLE TO DETECT THE PRESENCE OF A MICRO-ORGANISM IN A SAMPLE OR INSIDE A CONTAINER," which claims priority from French Patent Application Number 1355394 filed Jun. 11, 2013, both of which are incorporated herein by reference in their entirety.

TECHNICAL FIELD

The invention relates to a device, a system and a method of detection making it possible to detect the presence of a microorganism in a sample located inside a container, said sample being in contact with a culture medium, and capable of containing a microorganism. The presence of a microorganism is determined depending on the appearance of a potential microbial growth inside the container. The presence of such a microbial growth may be manifested, for example, by the appearance of cloudiness within the culture medium.

STATE OF THE ART

The possibility of observing the appearance of a potential microbial growth inside the container may prove useful for a wide variety of industrial and biological procedures, notably concerning sterility tests for procedures used in the production of pharmaceutical products.

The "Media Fill Test" (MFT) is an example of a prior art test concerning methods of observing the appearance of a potential microbial growth. This test, within the pharmaceutical industry makes it possible to verify whether methods for manufacturing sterile products are executed free from any threat of microbiological contamination.

Thus, if microbiological contamination of a supposedly sterile product occurs during execution of a method for obtaining the sterile product, this contamination is subsequently detected upon culturing the supposedly sterile product.

The MFT technique also makes it possible to verify, upon checking for a potential microbial contamination, whether the protocols followed by the personnel are complied with, and above all effective in preventing potential microbial contamination.

One of the particularities of the MFT consists in the methods for manufacturing sterile products imposing the shape and size of the container, the contents of which comprise the sample and the culture medium. Thus, the container in which a potential appearance of a microbial growth may be observed may come in various dimensions and shapes.

For this reason, the automation using the MFT of the procedures for monitoring a potential microbial growth in the containers, requires an adaptation of each test procedure to the dimensions and shape of the container concerned, causing a considerable loss of time.

In the prior art, inspection of products subjected to procedures and protocols aimed at ensuring the perfect sterility of said products is performed by a technician, who observes the contents at intervals, for the purpose of detecting the appearance of a microbial growth.

The presence appearance of a microbial growth may be manifested by the presence of a turbidity inside said contents. Turbidity is an example of an analysis criterion or parameter representing microbial growth. Another criterion often used is the appearance or disappearance of the fluorescence of a fluid. If the microbial growth criterion used is observation of disappearance of fluorescence, the technician must, at regular intervals, note his/her observations and perform operations aimed at checking for the potential presence of said fluorescence inside the container. The deployment of the technician represents a constraint if more than one inspection operation involving various containers need to be performed.

Pharmaceutical industry players have recently recognised that it would be highly advantageous to be able to monitor the evolution of potential microbial growth on a continuous basis. This monitoring could be implemented with computerized traceability of the results and computerized management of the appearance of cloudiness for a large number of tests.

Furthermore, it proves necessary to reduce or eliminate container handling in order to facilitate the test procedures.

In addition, the current observation of this potential microbial growth is based on a single analysis criterion or parameter for the same observation. It proves necessary to enable the detection of a microbial growth based on at least two analysis criteria or parameters during the same observation, in order to improve the reliability of observation of the microbial growth.

Devices and systems already known within the prior art make it possible to monitor a potential microbial growth inside a vessel.

A first type of system known within the prior art is disclosed within the American Patent Application US 2005/0266516. This system comprises an analysis container designed to receive a fluid in order to detect the presence or absence of fluorescence, or for observation of the evolution of the turbidity of said fluid over time. The operation of the system according to document US 2005/0266516 is based on the association of the analysis container with a specific container support suitable for receiving the analysis container. Thus, if a fluid to be analysed is contained within a first container, the fluid must be transferred to a second specific container, such as the analysis container, so that the analysis can be performed, using the container support, to observe a potential microbial growth. The container support comprises in its interior light sources and detection means, in order to detect the presence of fluorescence, the absence of fluorescence or the presence of turbidity within the analysis container. Consequently, the system according to document US 2005/0266516 requires use of a specific container such as the analysis container pre-formed to be suitable for the shape and dimensions of the container support. Therefore, such a system entails transfer of the fluid to be analysed from a first container to a second container. Use of such a system is not suitable for an MFT. Indeed, the transfer of a fluid from a first container to a second container is extremely detrimental to the sterility of the fluid, as the risk of microbiological contamination during the fluid transfer is high.

Similarly, a second type of system known from the prior art is disclosed within U.S. Pat. No. 6,723,554. This second system comprises an analysis container designed to receive a fluid in order to detect the presence or absence of fluorescence, or for observation of the evolution of the turbidity of said fluid over time. The operation of the system according to document U.S. Pat. No. 6,723,554 is based on the association of the analysis container with a container support specifically suitable for receiving the analysis container. Thus, if a fluid to be analysed is contained within a first container, the fluid must be transferred to a second specific container, such as the analysis container, so that the analysis can be performed to observe a potential microbial growth. The container support is pre-formed in order to enable the insertion of a light source and a detection means from outside of the wall of the container support to the container wall. Consequently, the system according to document U.S. Pat. No. 6,723,554 requires use of a specific container such as the analysis container, with a shape and dimensions specifically suitable for the shape and dimensions of the container support. Therefore such a system also entails transfer of the fluid to be analysed from a first container to a second specific container such as the analysis container.

As with the first type of prior art system, the second type of prior art system requires transfer of the fluid to be analysed from a first container to a second container which has a suitable shape and dimensions to match the shape and dimensions of a container support required for the fluid analysis.

Thus, such systems lead to an increased risk of contamination during the fluid analysis method. Therefore it proves necessary to enable the analysis of a fluid using one single container.

In addition, such systems are suitable only for one specific type of container. Thus, when a large number of analyses need to be performed, the analysis costs related to the production of identical containers are high. Therefore it also proves necessary to enable the analysis of a fluid within a container, whatever the shape and/or dimensions of the container, in order to limit the costs related to implementing the fluid analysis method.

OBJECT OF THE INVENTION

With reference to the observations above, one objective of the present invention consists in providing a device, system and method of detection for detecting the presence of a microorganism in a sample located inside a container, said sample being in contact with a culture medium, and capable of containing a microorganism, whilst avoiding the problems and disadvantages associated with the devices, methods and systems relating to the prior art.

Another objective consists in providing a device, a system and a method of detection thanks to which a potential microbial presence may be detected inside a variety of containers, whatever the shape and dimensions of these containers.

Another objective consists in providing a device, a system and a method of detection enabling the detection of a microbial presence inside a container, without interrupting the implementation of the method.

SUMMARY OF THE INVENTION

Thus, according to a first aspect of the invention, the present invention concerns a device for detecting the presence of at least one microorganism in the contents of a container comprising a wall with a translucent zone, said detection device comprising:

a) at least one light source, such as a light-emitting diode (LED), capable of illuminating the contents of the container by emitting an excitation light beam through the translucent zone of the container;

b) at least one detection means, such as a photodiode, for detecting at least one reaction light beam emitted in response to the illumination of the contents of the container;

said at least one light source and said at least one detection means being equipped with at least one connection means located entirely outside of the container to connect said at least one light source and said at least one detection means to the container wall, in the translucent zone, said connection means making it possible to adapt the position of the detection device on the container wall, said at least one detection means being positioned at an angle of set value in relation to the direction of the excitation light beam, to detect the reaction light beam.

Advantageously, the detection means comprises at least a first and a second photodetector, positioned respectively in a first and a second site to detect, in the translucent zone of the container, a first and a second reaction light beam, in order to obtain a first and a second value of an analysis parameter representative of a potential microbial presence in the contents of the container.

Advantageously, said at least one detection means comprises a first photodetector suitable for detecting a first reaction light signal, in order to obtain a value n of a first analysis parameter representative of a potential microbial presence in the contents of the container, and a second photodetector suitable for detecting a second reaction light beam, different from the first reaction light beam, in order to obtain a value m of a second analysis parameter representative of a potential microbial presence in the contents of the container.

Advantageously, the first photodetector comprises a red-filtered photodiode and the second photodetector comprises a green-filtered photodiode.

Advantageously, the detection system comprises a detection device according to the present invention and a control device connected to said at least one light source and to said at least one detection means to control the excitation light beam emitted by said at least one light source, and process and/or analyse said at least one reaction light beam emitted in response to the illumination of the contents of the container, and detected by said at least one detection means.

Advantageously, the control device comprises:
  a storage medium for storing a first value of the first and second analysis parameters obtained with at least one detection means, and a second value of the first and second analysis parameters obtained after a set time period with at least one detection means,
  a comparison means for comparing the first and second values of the first and second analysis parameters, to determine a potential microbial growth in the contents of the container.

Advantageously, the control device is suitable for receiving and storing values obtained with said at least one detection means, on a continuous basis.

Advantageously, the control device comprises an alarm, to indicate a potential microbial presence in the contents of the container.

According to a second aspect of the invention, the present invention concerns a method for detecting the presence of at least one microorganism in a sample capable of containing said at least one microorganism, said method comprising the following steps:

a) introducing the sample into a container comprising a wall with at least one translucent zone, said sample being placed in contact with a culture medium prior to introduction or after introduction of said sample into said container, said at least one culture medium being suitable for enabling the growth of said at least one microorganism, the mixture of the sample and said culture medium forming all or part of the contents of the container, b) potentially incubating the container at a temperature and for a time period sufficient to enable growth of said at least one microorganism, c) measuring, using a detection system according to the present invention at least one value n of at least one analysis parameter representative of a potential microbial presence inside the container, step c) comprising the sub-steps consisting in:
    c1) illuminating the contents of the container through the translucent zone with the light source and,
    c2) detecting the reaction light beam emitted in response to the illumination of the contents with said at least one detection means, in order to obtain said value n of the analysis parameter, d) comparing said value n with a threshold value ns of the same analysis parameter, said threshold value ns being indicative of the presence of at least one microorganism in the sample, e) deducing the presence or absence of said at least one microorganism, within the sample, based on the result of the comparison.

Preferably, step b) consists in incubating the container at a temperature and for a time period sufficient to enable growth of said at least one microorganism.

According to a particular embodiment of the method according to the present invention,
    step c) comprises measuring at least one analysis parameter, the value n of which increases as the quantity of said microorganism increases, such as for example turbidity,
    step d) comprises comparing said value n with a threshold value ns of the same analysis parameter, said threshold value ns being indicative of the presence of at least one microorganism in the sample,
    step e) comprises deducing the contamination of the sample by at least one microorganism if the value n is equal to or greater than the threshold value ns.

According to a variant of the particular embodiment of the method according to the present invention:
    step c) comprises measuring at least one analysis parameter, the value n of which decreases as the quantity of said microorganism decreases, such as for example fluorescence,
    step d) comprises comparing said value n with a threshold value ns of the same analysis parameter,
    step e) comprises deducing the contamination of the sample by said at least one microorganism if the value n is less than or equal to the threshold value ns.

According to a variant of the particular embodiment of the method according to the present invention:
    step c) comprises measuring at least a first analysis parameter, a value n1 of which increases as the quantity of said microorganism increases, such as for example turbidity, and measuring at least a second analysis parameter, a value n2 of which decreases as the quantity of said microorganism decreases, such as for example fluorescence,
    step d) comprises comparing said value n1 with a threshold value ns1 associated with the first analysis parameter, and comparing said value n2 with a threshold value ns2 associated with the second analysis parameter,
    step e) comprises deducing the contamination of the sample by said at least one microorganism if the value n1 is equal to or greater than the threshold value ns1 and if the value n2 is less than or equal to the threshold value ns2.

According to a third aspect of the invention, the present invention concerns the use of a detection system according to the present invention to detect the presence of at least one microorganism in the contents of a container comprising a wall with a translucent zone.

According to the present invention, the sample may be from various origins, for example of food, environmental, veterinary, clinical, pharmaceutical or cosmetic origin.

Amongst the samples of food origin, non-exhaustive mention can be made of a sample of dairy products (yogurts, cheeses, etc.), meat, fish, egg, fruit, vegetable, water, beverages (milk, fruit juice, soda, etc.). Of course, these samples of food origin can also come from sauces or more complex meals, or from unprocessed or partially processed raw materials. A sample of food origin can also come from an animal feed, such as oil cakes, animal meals.

As indicated previously, the sample can be of environmental origin and can consist, for example, of a surface specimen, water specimen, air specimen, etc.

The sample can also consist of a sample of clinical origin, which can correspond to specimens of biological fluid (urine, whole blood or derivatives such as serum, saliva, pus, cerebrospinal fluid, etc,), of stools (for example cholera-induced diarrhoea), of specimens from the nose, throat, skin, wounds, organs, tissues or isolated cells. This list is obviously not exhaustive.

Preferably, the sample is of pharmaceutical origin, and corresponds for example to pharmaceutical preparations or vaccine preparations.

Generally, the term "sample" refers to a part or a quantity, more particularly a small part or a small quantity, sampled from one or more entities for the purpose of analysis. This sample can possibly have undergone a pretreatment, involving for example mixing, dilution or even crushing stages, in particular if the starting entity is solid-state.

The sample collected is, in general, capable of—or suspected of—containing at least one target microorganism, and mainly a bacterium.

The term "microorganism" has the same meaning as that generally accepted in microbiology and comprises notably Gram-positive or Gram-negative bacteria, yeasts, moulds and more generally, single-cell organisms, invisible W the naked eye, which can be manipulated and multiplied in a laboratory.

Advantageously, the sample is placed in contact with at least one culture medium enabling the growth of the microorganisms and, in particular of the target microorganism(s). "Culture medium" is to be understood to be a medium comprising all the elements necessary for the survival and/or for the growth of the microorganisms and, in particular, of the microorganisms sought (for example buffered peptone water). The culture medium may contain possible additives, for example: peptones, one or more growth factors, carbohydrates, one or more selective agents, buffers, one or more vitamins, etc.

For the purposes of the present invention, the term "beam" used notably in the expressions "excitation light beam" or "reaction light beam" designates one or more beams comprising one or more light rays.

BRIEF DESCRIPTION OF THE DRAWINGS

The invention shall become more clearly apparent upon reading the following description, with reference to the corresponding figures, which depicts, by way of non-limiting examples, a method and a system according to the present invention. More precisely:

FIG. 2 represents the detection device according to the invention, fixed onto the external wall of a container of a first diameter, positioned substantially vertically, according to a first embodiment of the invention;

FIG. 3 shows the detection device, according to FIG. 2, fixed on a container of a second diameter;

DETAILED DESCRIPTION OF THE INVENTION

Figure 1:
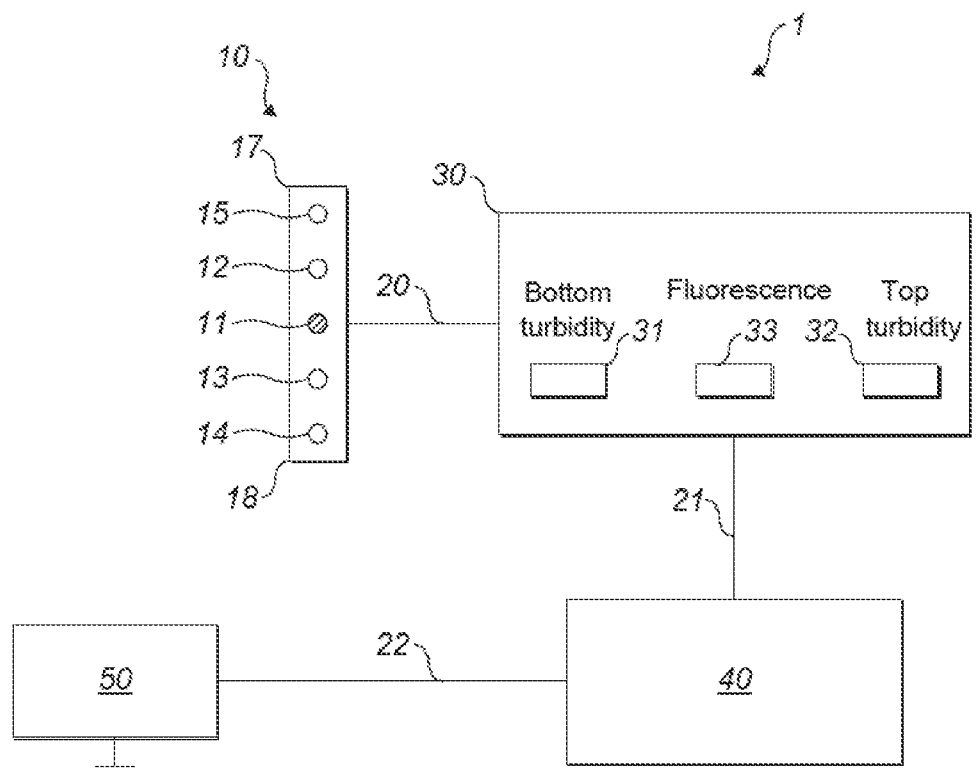
FIG. 1 shows, schematically, a detection system comprising a detection device according to an embodiment of the invention.

FIG. 1 shows, schematically, the various elements of a first embodiment of a detection system 1 for performing the detection method according to the present invention. The detection system 1 comprises a detection device 10, suitable for being fixed on the external wall of a container, the functionalities of which are described in detail below.

Within the detection system 1 according to the invention, the container contains notably a culture medium and a sample to be observed. Alternatively, the sample may be placed in contact before being introduced into the container.

The container is suitable for enabling the application of the detection method according to the invention, and notably the observation, inside the container, of a potential microbial growth. Thus, the container according to the invention is at least partially translucent, and therefore comprises a wall with at least one translucent zone. The translucent nature of the container wall is necessary to allow the passage of an excitation light beam, from outside the container to the inside of the container. As described below, the reaction light beam, generated inside the container in response to the excitation light beam, must be detected in order to be captured and measured by a sensor, such as a photodiode type photodetector, outside of said container. The translucent nature of the wall of the container used in the detection method, and within the detection system 1 according to the invention, may result from use of materials such as glass or plastic in the manufacture of said container. Advantageously, the container according to the invention comprises a wall with at least one transparent zone.

As shown in FIG. 1, within the detection system 1, the detection device 10 is connected, by means of a first wire connection 20, to a signal converter 30 in order to enable the conversion of an analogue signal into a digital signal. Thus, the signal converter 30 makes it possible to convert any analogue signal detected by the detection device 10 into a digital signal for analysis purposes. The signal converter 30 is marketed, for example, in the form of an acquisition kit by DATAQ™ Instruments, Inc. under reference DI-7188. The signal converter 30 comprises, for example, three conversion units 31, 32 and 33. Each conversion unit 31, 32 and 33 enables the conversion of a specific analogue signal detected by means of the detection device 10. Thus, the first conversion unit 31 makes it possible, for example, to convert the analogue signal associated with the presence or absence of turbidity at a first specific point inside the container under observation. A second conversion unit 32 makes it possible, for example, to convert the analogue signal associated with the presence or absence of turbidity at a second specific point inside the container under observation. A third conversion unit 33 makes it possible, for example, to convert the analogue signal associated with the presence or absence of fluorescence of the fluid observed. The signal converter 30 is connected, by means of a wire 21, to a power source 40. The power source 40 comprises for example batteries such as two Li batteries, AA format (2600 mAh). The assembly comprising the detection device 10, the signal converter 30 and the power source 40, is itself connected to a control device 50, such as a computer, by means of a wire connection 22.

The control device 50 enables various functions to be performed. The functions consist notably in processing, analysing and comparing the various digital signals transmitted by the signal converter 30 derived from detection of reaction light beams, as described below, by means of the detection device 10. The processing of the digital signals comprises notably receiving and storing the digital signals associated with detection of the reaction light beams. Another function of the control device 50 consists in setting the technical parameters of the various elements present in the detection device 10 when using the system 1 according to FIG. 1. These technical parameters comprise, for example, threshold values set concerning the presence or absence of turbidity, and the presence or absence of fluorescence. Thus, according to the value of the signal detected during the sample analysis method, an alert signal can be emitted, passively for a user, in order to indicate to the user the presence of microbiological contamination depending on whether the value corresponding to the signal detected is less than or greater than the threshold value concerned. Therefore no active monitoring of the signals by a user is required.

The detection device 10 is suitable, as shown in FIGS. 2, 3, 4, 5 and 7, for being fixed to the external wall of a container 100, 200 and for enabling observation of modifications relating to the contents inside said container 100, 200. The nature and site of the various elements of the detection device 10 according to the invention make it possible to optimise monitoring of the transformation of the contents associated with a potential microbial growth developing in the contents of the container 100, 200.

The detection device 10 is equipped with a light source 11 producing an excitation light beam. The light source 11 comprises, for example, a light-emitting diode (LED) 3 mm in diameter. An LED of this type may represent a spectrum centred on 557 nm, with a width at mid-height of 22 nm. Such an LED is marketed, for example, by SIEMENS™ under reference LP3440.

An electronic module (not shown), such as a constant-current excitation electronic circuit, may be adjoined to the detection device 10 to perform the control function for the light source 11, and notably the configuration of the parameters relating to the emission of the excitation light beam, such as the intensity or duration of emission of the light source. The constant current applied is, for example, 15.6 mA and the amplification of the photocurrents is such that $U=10^9 I$, where I represents the intensity. This electronic module may also be integrated into the control device 50.

The detection device 10 is also equipped with at least one means of detection such as a photodetector type sensor. The detection means comprises a first photodetector 12, such as a photodiode 12, which is specifically used for observing a first analysis parameter such as the fluorescence of a fluid inside the container 100, 200. The photodiode 12 is equipped with a "red" filter in order to enable the observation of the fluorescence of a fluid inside the container 100, 200. For example, the photodiode 12 is a broad spectrum photodiode red-filtered by means of a so-called "dichroic band-pass filter", presenting a spectrum of greater than 610 nm. The photodiode 12 is characterised by a relatively closed viewing angle, at +/−15°, and a low dark current at 20 pA. This type of photodiode is marketed, for example, by PERKIN ELMER under reference VTB 1113.

The light source 11 enables transmission of a certain quantity of light toward the inside of the container 100, 200. In the presence of a microbial growth, a reaction light beam generated inside the contents of the container 100, 200 may be captured using the first photodiode 12. As indicated in detail below, the detection of the fluorescence emitted by a fluid represents a first possibility for observing a potential microbial growth within the fluid located inside the container 100, 200.

The detection means comprises a second photodetector 13, or photodiode 13, used for observing the turbidity of the contents of the container. The photodiode 13 is equipped with a "green" filter in order to enable the observation of a second analysis parameter such as fluid turbidity. For example, the photodiode 13 is a broad spectrum photodiode green-filtered by means of a so-called "dichroic band-pass filter", presenting a spectrum of 500 to 570 nm. The photodiode 13 is characterised by a relatively closed viewing angle, at +/−15°, and a low dark current at 20 pA. This type of photodiode is marketed, for example, by PERKIN ELMER under reference VTB 1113. The quantity of light derived from the reaction light beam and stored by the photodiode 13 equipped with the "green" filter indicates the potential appearance of cloudiness in the contents of the container 100, 200. The cloudiness is associated, for example, with the presence of solid particles within the fluid. The detection of turbidity represents a second possibility for detecting any microbial growth within the fluid located inside the container 100, 200.

The turbidity measurement using a light source and at least one detection means such as photodetectors is associated with the fact that when matter is exposed to electromagnetic rays, these electromagnetic rays interact with the electronic charges of the atoms. Some of the rays pass through the matter without their direction being modified. Other rays are diffused in all directions. This means that each illuminated particle behaves like a punctiform light source. For this reason, the quantity of light diffused by the particles present inside of a fluid increases with the quantity and size of said particles. In addition, when these particles are microorganisms, we can observe that light diffusion does not appear homogeneous in all directions, but predominantly in a similar direction to the light rays emitted by a light source. Thus, the arrangement of the light source and of at least one detection means on the same side outside of the container 100, 200 and on the same side of the container wall, with a set distance between the light source and detection means, makes it possible to optimise turbidity detection within the contents of the container 100, 200, as set out below.

As indicated in FIG. 1, the detection device 10 is equipped with an upper end 17 and a lower end 18. The detection means is equipped with a third photodetector 14, or third photodiode 14, positioned relatively close to the lower end 18 of the detection device 10. The photodiode 14 is, for example, green-filtered. The photodiode 14 may be suitable for observing events at a specific point of the container 100, 200, such as a microbial growth located in the vicinity of the bottom of the container 100, 200 if the detection device 10 is fixed onto said container 100, 200. The detection device may be equipped with a fourth photodetector 15, or fourth photodiode 15, suitable for specific detection depending on the fluid observed by means of the detection device 10.

As indicated above, the light source 11 is used to direct, inside of the container 100, 200, a certain quantity of light or excitation light beam for the purpose of generating a reaction light beam inside the contents present in the container 100, 200. Therefore the detection means 12, 13, 14, 15 makes it possible to detect at least one reaction light signal emitted by the contents of the container 100, 200, in order to monitor a potential microbial growth inside the container 100, 200 to determine the microbiological contamination of the sample associated with the presence of at least one microorganism.

Generally, the various photodetectors 12 to 15 of the detection means notably possess a function making it possible to add filters so as to be able to receive light beams with a specific wavelength.

The operation of the detection system 1 according to FIG. 1 is described below with reference to FIGS. 2, 3 and 4.

Figure 4:
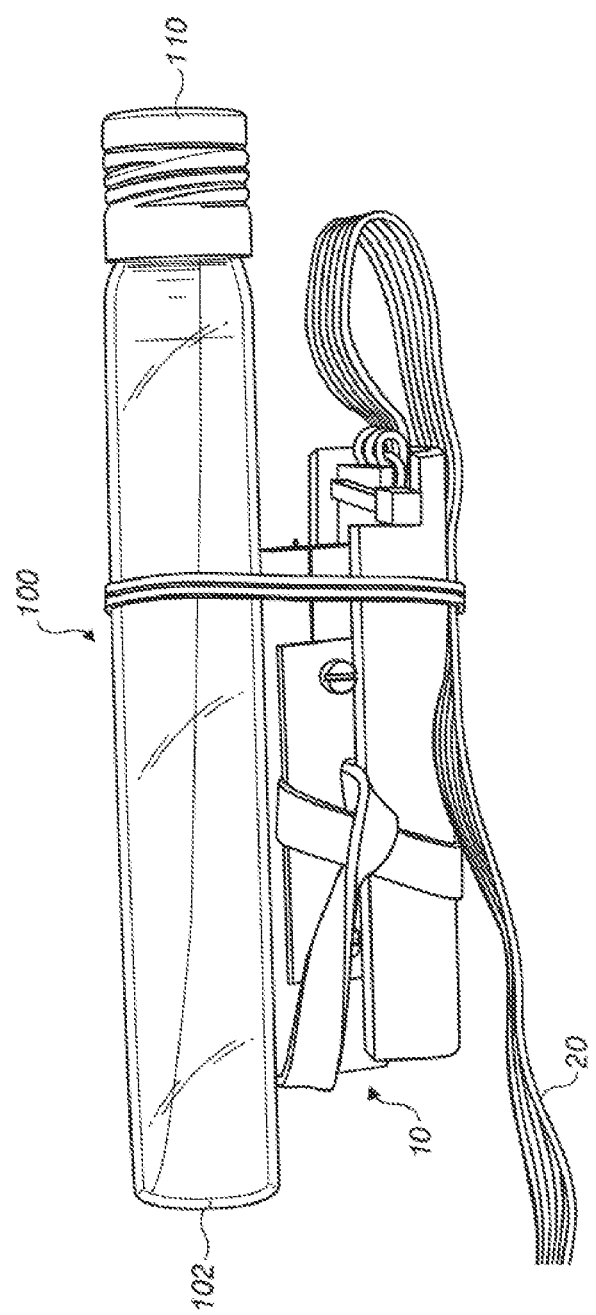
FIG. 4 represents the detection device, according to FIGS. 2 and 3, used with the container of a first diameter positioned substantially horizontally.

FIGS. 2, 3 and 4 show a container 100, 200, equipped with a stopping means 110, 210 such as a plug, said container 100, 200 containing contents 101, 201 such as a fluid. The contents 101, 201 comprise a culture medium suitable for optimising microbial growth. In FIG. 3, the container 200 has a diameter greater than the diameter of the container 100 according to FIG. 2.

As shown in FIGS. 2, 3 and 4, the detection device 10 is positioned on and connected to the outside of the container 100, 200. This means that it is possible to observe microbial growth inside the container 100, 200, without being forced to introduce an observation means inside said container 100, 200.

As shown in FIGS. 2, 3 and 4, the detection device 10 is fixed on the outside of the container 100, 200, such that said detection device 10 detects a potential microbial growth within the contents 101, 201 of the container 100, 200. The detection device 10 is fixed on the external wall of the container 100, 200 using any suitable connection means 105, 205, for example using an elastic band. The connection means 105, 205 makes it possible to connect the detection device 10 directly to the wall of the container 100, 200 so that the distance between the detection device 10 and the wall of the container 100, 200 is as small as possible. The connection means 105, 205 can also make it possible to connect the detection device 10 while maintaining a set distance from the wall of the container 100, 200. The set distance corresponds to a free space, of around a few centimeters, so that the detection device 10 and the wall of the container 100, 200 are not in contact. Therefore the detection device 10 according to the invention presents the advantage of being connected to the outside of the container 100, 200 on the wall of the container 100, 200 or in the vicinity of the wall of the container 100, 200, whatever the shape of said container 100, 200, using the connection means 105, 205. This advantage makes it possible to use the detection device 10 for observing a microbial growth inside any type of container, i.e. whatever the shape and size of the container.

Thus, contrary to the methods disclosed in the prior art, when the MFT is finalised, there is no need to transfer the contents 101, 201 of the container 100, 200 comprising the biological sample to another container specifically suited for use in a particular analysis device.

In the rest of the description of FIGS. 2, 3 and 4, reference is made to use of the detection system 1 according to the invention, in particular to analyse the contents of a container 100, 200 obtained at the end of a "Media Fill Test" (MFT).

When using a detection device 10 such as shown in FIG. 2, upon introduction of said sample into the contents 101, microbial growth may be observed using the detection system 1 according to the invention.

Generally, with reference to FIGS. 2, 3, 4 and 6, the light source 11 and detection means 12, 13, 14, 15 are placed outside of the container 100, 200. In order to optimise detection of the reaction light beam from the contents 101 of the container 100, 200 by the detection means 12, 13, 14, 15, the light source 11 and detection means 12, 13, 14, 15 must be placed in the translucent zone of the container 100, 200, i.e. sufficiently close to the translucent zone to enable the excitation light beam emitted by the light source 11 to be emitted through the translucent zone and the reaction light beam from the contents of the container 100, 200 to be detected by the detection means 12, 13, 14, 15. Thus, the light source 11 and detection means 12, 13, 14, 15 are located in the translucent zone of the wall of the container 100, 200. The detection means 12, 13, 14, 15 is positioned at an angle of a set value in relation to the direction of the excitation light beam. Thus, the detection means 13, 14, 15, can optimally detect the reaction light beam generated by the contents 101 of the container 100, 200. The set angle values are between 0° and 180° inclusive. Advantageously, the set angle values are between 0° and 90° inclusive. Particularly advantageously, the set angle value is between 0° and 30° inclusive. The angle value may also be substantially equal to 0°. In addition, the distance between the light source 11 and the detection means 12, 13, 14, 15 is generally in the order of a few centimeters, in order to guarantee relative proximity between the light source 11 and the detection means 12, 13, 14, 15 when the detection device 10 is in operation.

Within the detection device 10 as shown in FIG. 2, the light source 11 and detection means 12, 13, 14 and 15, shown in FIG. 1, are arranged, advantageously, so as to be aligned with the outside of the container 100 insofar as the detection device 10 is fixed on the wall of the container 100.

When the invention is in use, as shown in FIG. 2, the container 100 is used in a vertical position, the bottom 102 of said container 100 itself being mounted on a support. The detection device 10 according to the invention is fixed on the outside of the container 100 in order to be positioned as close as possible W the bottom 102 of the container 100. In this position, the photodiode 14, positioned as low as possible, as shown in FIG. 1, is specifically suited for enabling the monitoring of a potential microbial growth inside the container 100, near the bottom 102. A protective cover 2 may be added in order to protect the various elements of the detection device 10 from potential damage.

The detection device 10 according to the invention is represented in FIG. 3, without the protective cover 2 shown in FIG. 2, in order to show the interior part of the detection device 10, which, notably, comprises an electronic card 203 equipped with various electronic components. The electronic card 203 is suitable for receiving instructions transmitted from the control device 50, shown in FIG. 1, and transmitting these instructions to various elements, notably to the light source 11 and the detection means 12, 13, 14 and 15, thanks to the wire connections 20, 21 and 22.

FIG. 4 describes an embodiment wherein the container 100, according to FIG. 2, is used in a substantially horizontal position, with the stopping means 110 and the bottom 102 positioned substantially on the same horizontal plane. The particular position of the container 100 makes it possible, for example, to detect the presence of germs, observing the presence of a sedimentation layer of these germs.

Figure 5:
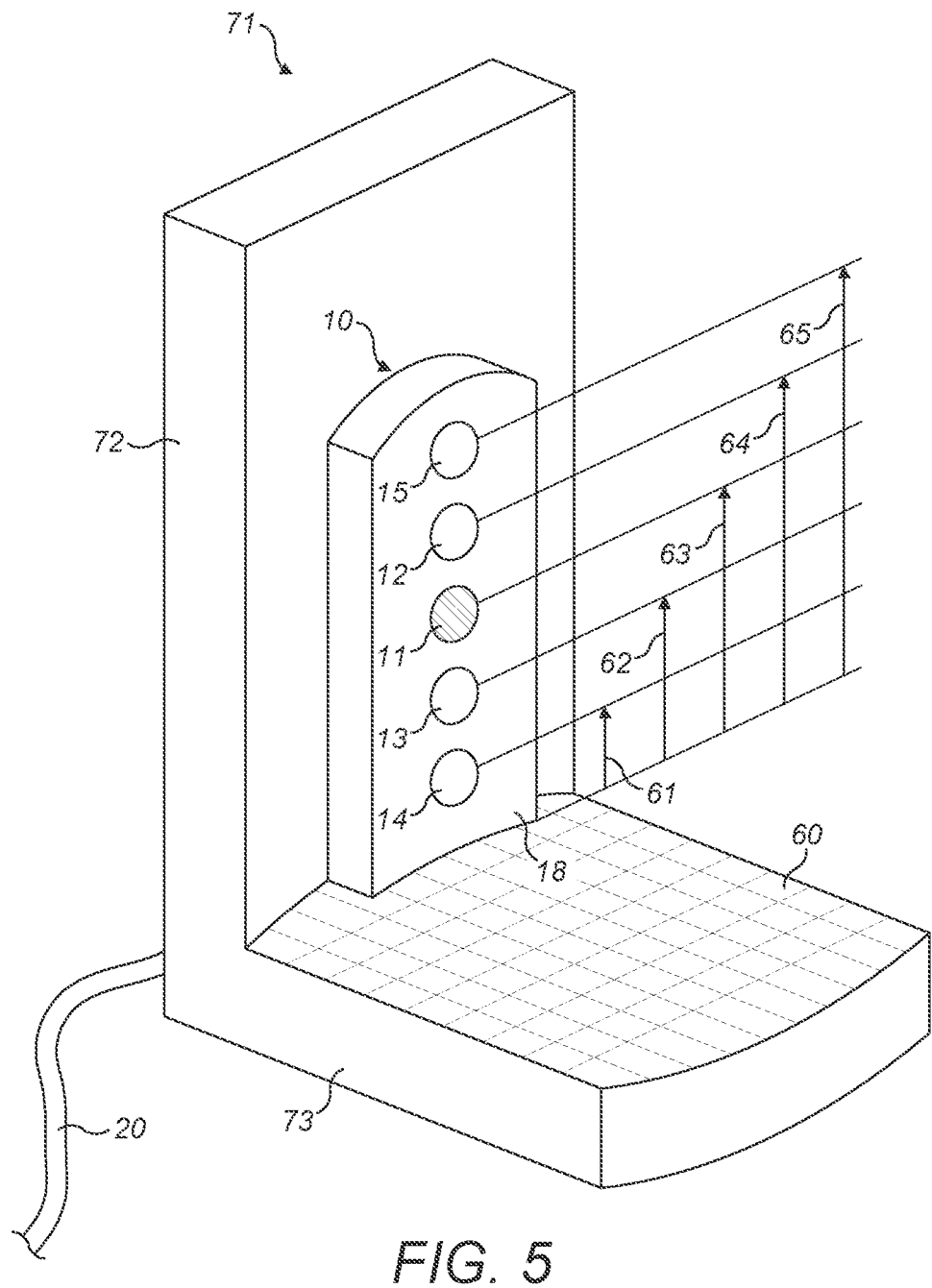
FIG. 5 shows the detection device according to a second embodiment of the invention.

According to a third embodiment, FIG. 5 shows a support device 70 comprising an "L"-shaped base 71, presenting a first part 72 and a second part 73 comprising a surface 60. As represented in FIG. 5, the detection device 10 is integrated into the first part 72.

A container of any size or dimensions can be positioned on the surface 60 of the second part 73 of the base 71 so that the surface of the container bottom is superimposed over the surface 60. Thus, using the detection device 10 as per FIG. 5, the distance between the bottom of the container and the elements 11, 12, 13, 14 and 15 represents a fixed distance. In FIG. 5, the fixed distance is indicated using arrows 61 to 65. The fixed distance makes it possible to identify with precision the site of a container, in order to place another container under the same test conditions when analysing the contents of this other container. Therefore the base 71 makes it possible to reproduce with precision particular conditions relating to the test, whatever the container type.

Figure 6:
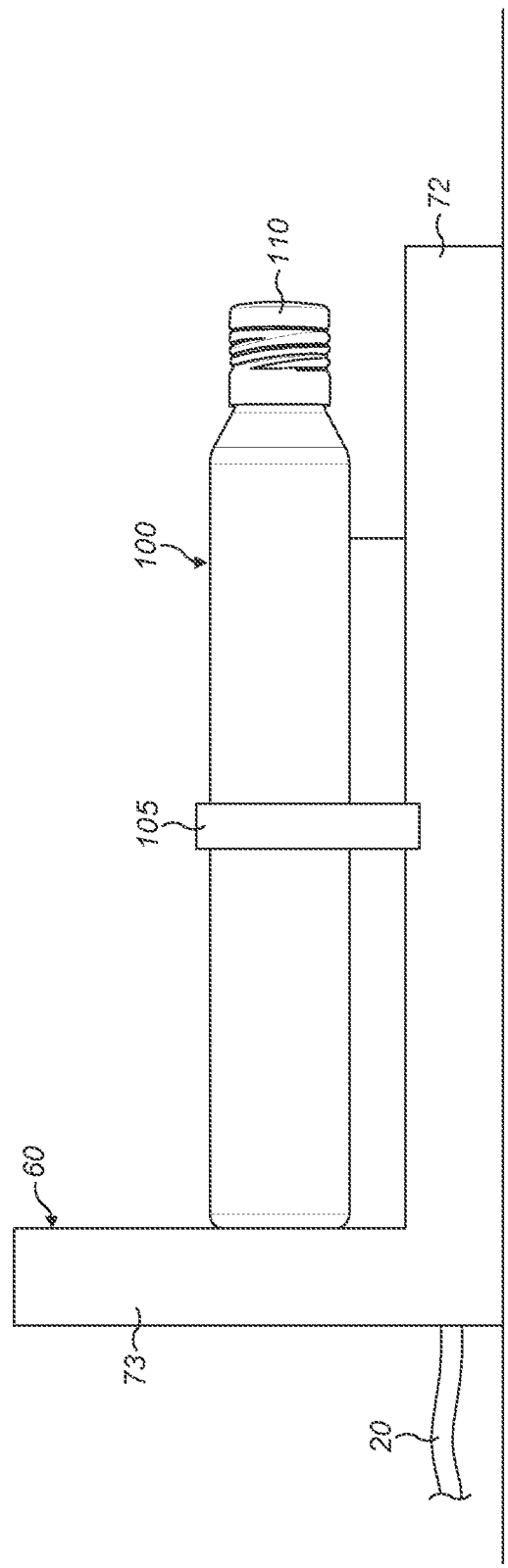
FIG. 6 represents the detection device, according to FIG. 5, used with the container of a first diameter positioned substantially horizontally.

FIG. 6 represents the support device according to FIG. 5 used in combination with a container 100, said container 100 being arranged in a substantially horizontal position. The bottom of the container 100 is in contact with the surface 60 of the second part 73 of the base 71. The fixed position of the container 100 on the device is ensured thanks to the connection means 105. In this position, the user can easily detect potential solid particle deposits associated with the existence of a fluid turbidity.

Figure 7:
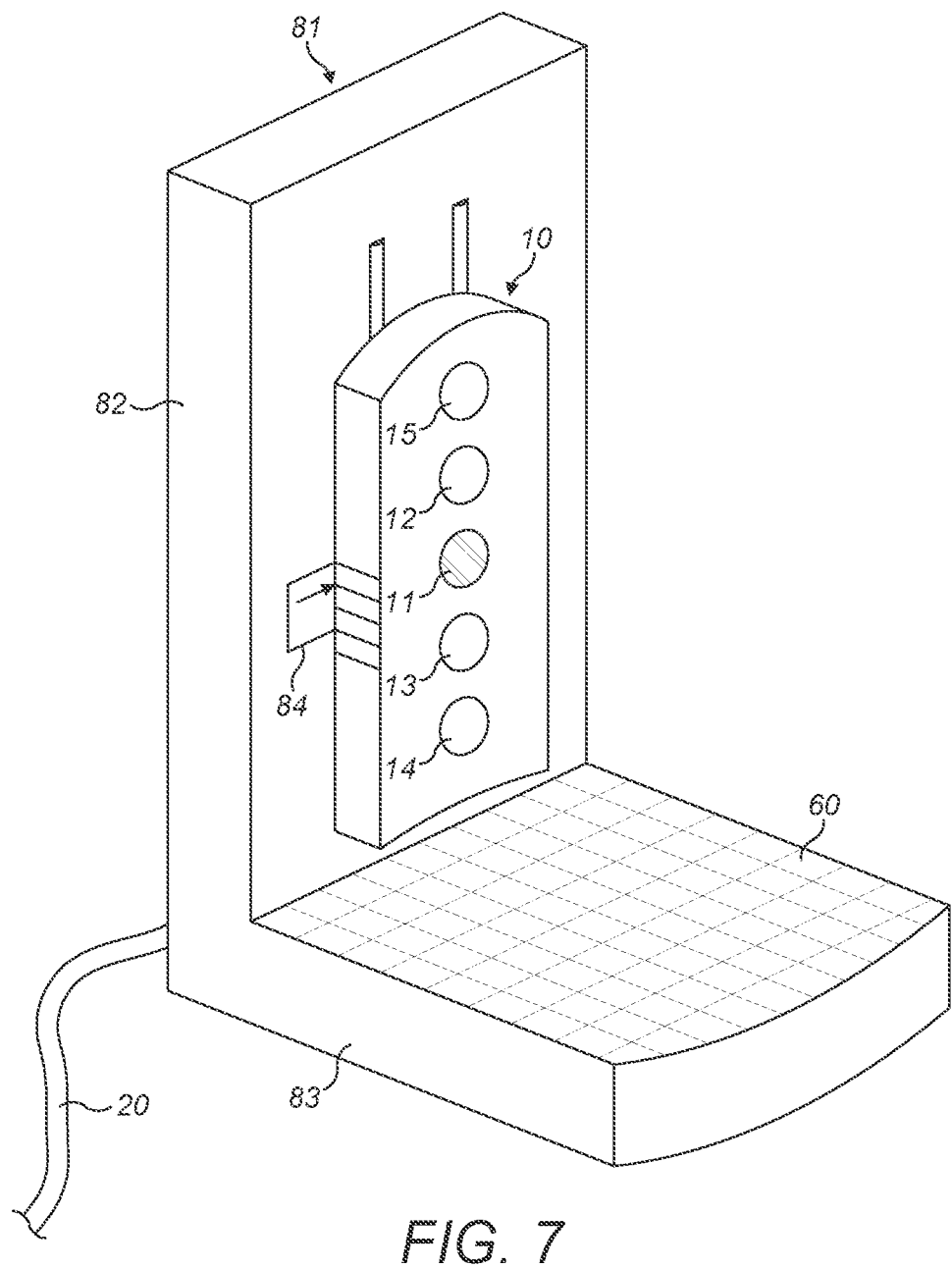
FIG. 7 shows the detection device according to a third embodiment of the invention.

According to a variant of the third embodiment of the invention, FIG. 7 shows a support device comprising a base 81, comprising a first part 82 and a second part 83. The detection device 10 is fixed on the second part 82 of the base 81. According to FIG. 7, the distance between the detection device 10 and the surface 60 is adjustable. This means that the detection device 10 can be placed in a suitable position referenced using an indicator 84 before positioning a container on the surface 60. Since the support device according to FIG. 7 is adjustable, the user can easily adapt the constraints due to the shape of the container to optimise the implementation of the test.

The detection system 1 operates according to a detection method comprising the following steps.

Thus, a first step comprises the introduction of a sample into a container 100, 200 comprising a wall with at least one translucent zone. The sample is capable of containing at least one microorganism. Therefore the sample is placed in contact with a culture medium suited to enable growth of the microorganism. The mixture of the sample and said culture medium forms all or some of the contents 101, 201 of the container 100, 200. The sample may be placed into contact with the culture medium either prior to introducing the sample into the container 100, 200, or after introducing the sample into the container 100, 200.

The detection method comprises an optional second step, comprising incubating the container 100, 200 at a temperature and for a time period sufficient to allow the growth of said at least one target microorganism. Advantageously, the detection method comprises this incubation step.

A third step comprises illuminating the contents of the container 100, 200 through the translucent zone with the light source 11, which emits an excitation light beam.

A fourth step comprises the detection using the detection means 12, 13, 14, 15 of at least one reaction light beam emitted in response to the illumination of the contents, i.e. the emission of the excitation light beam by the light source 11. The reaction light beam is associated with a detection by measuring an analysis parameter representative of a potential microbial presence inside the container 100, 200. The choice of analysis parameter depends on the type of detection desired. Thus, a first analysis parameter may concern turbidity and a second analysis parameter may concern fluorescence.

In a fifth step, the detection device 10 receives and transmits to the signal converter 30 the reaction light beam for conversion into a reaction digital signal. Thus, the signal converter 30 makes it possible to obtain a value n associated with the analysis parameter in question. Thus each value n is measured periodically for a specific duration, and is associated with a reaction light beam detected by the detection means 12, 13, 14, 15.

If the analysis parameter in question is turbidity, the various measured values n increase as the quantity of the microorganism within the contents of the container 100, 200 increases.

If the analysis parameter in question is fluorescence, the various measured values n may increase or decrease as the quantity of the microorganism within the contents of the container 100, 200 increases, depending on the nature of the microorganism.

A sixth step comprises comparing the measured value n with a threshold value ns of the same analysis parameter. The threshold value ns indicates the presence of at least one microorganism in the sample, and is associated with the analysis parameter in question.

In a seventh step, depending on the result of the comparison between the values n and ns, it is possible to deduce the presence or absence of at least one microorganism, within the sample.

Thus, if the analysis parameter concerns turbidity, the presence of the microorganism within the contents of the container 100, 200 is proven if the measured value n is equal to or greater than the threshold value ns for this same analysis parameter relating to turbidity.

If the analysis parameter concerns fluorescence, the presence of the microorganism within the contents of the container 100, 200 is proven if the measured value n is equal to or greater than the threshold value ns for the same analysis parameter, or if the measured value n is less than or equal to the threshold value ns for this same analysis parameter relating to fluorescence. The condition of the measured fluorescence value n, increasing or decreasing, depends on the nature of the microorganism sought.

The detection method may comprise a combination of detection steps relating to several analysis parameters, simultaneously.

Thus, the detection process makes it possible, according to an alternative embodiment, to measure n values associated with a first and a second analysis parameter. Thus, the measured n values are compared with the respective threshold values ns1 and ns2 of each analysis parameter. According to the result of the comparison step described above, it is possible to deduce the presence or absence of a microorganism within the contents 101, 201 of the container 100, 200.

This combination of analysis parameters to detect the presence of a microorganism within the contents of the container 100, 200 makes it possible to reliably validate the presence or absence of a microorganism.

Figure 8:
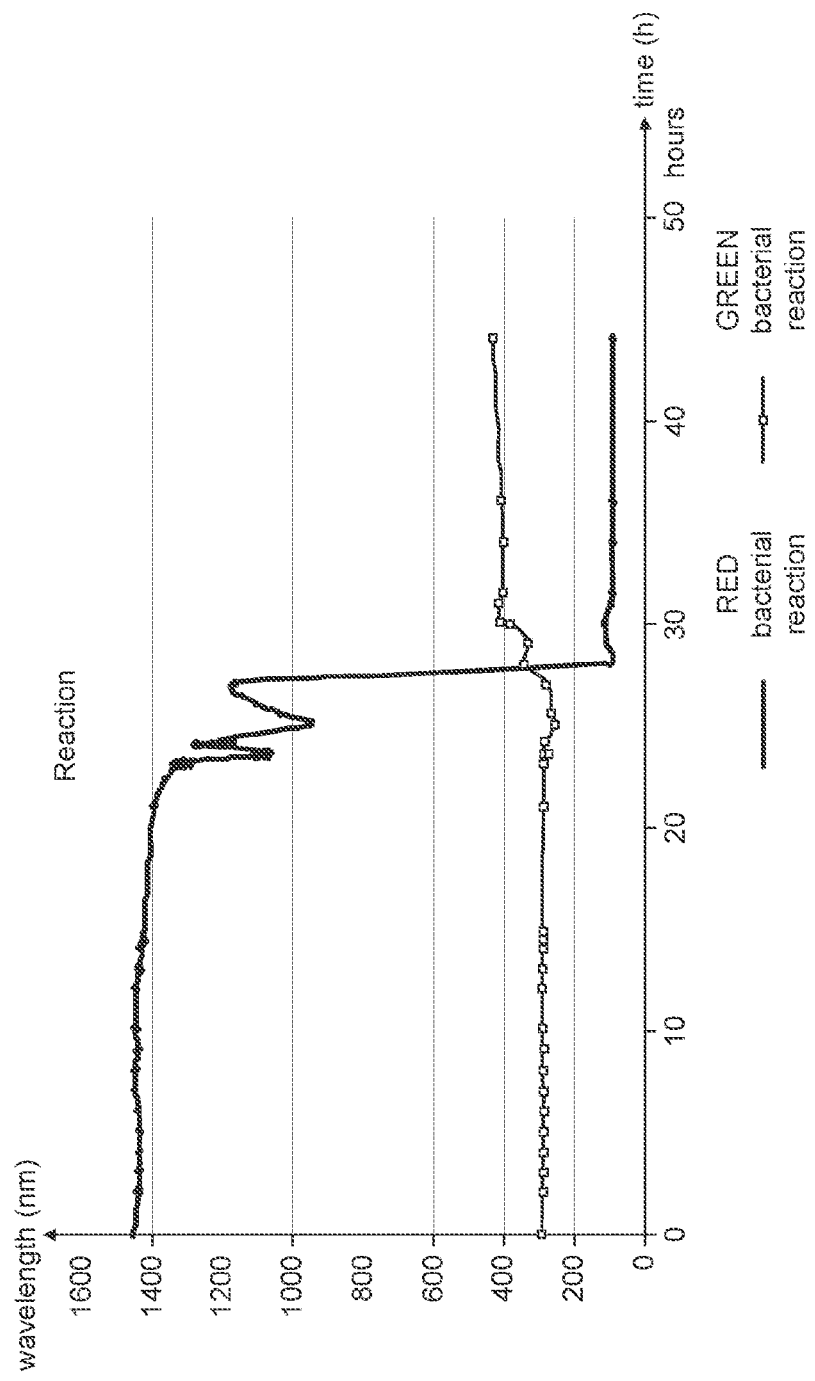
FIG. 8 represents results obtained using a detection system according to an embodiment of the invention, said results comprising a first reaction signal concerning a first analysis parameter associated with the disappearance of fluorescence within the container, and a second reaction signal concerning a second analysis parameter associated with the presence of turbidity within the container.

FIG. 8 represents the results of the observation of a vessel 100 containing a fluid 101 comprising a biological sample.

The detection device 10 according to the invention is used to reveal potential microbial growth inside a container 100 according to a first analysis parameter associated with the disappearance of fluorescence within the container 100.

As represented in FIG. 8, after a first incubation period of the order of 24 hours, it is possible to observe, concerning the photodetector 12 associated with the red bacterial reaction, the incipient development of microbial growth, giving rise to an oscillation of period 1 to 2 mins and of amplitude 2 to 3% of the level, with an average value decreasing by the order of 10% per hour. It is possible to observe an abrupt drop in the response, i.e. fluorescence inside the container, after an observation period of approximately 27 to 28 hours.

In FIG. 8, the signal obtained thanks to the photodiode 12 shows a drop from approximately 1300 to 90 nm. Therefore the photodiode 12 makes it possible to observe the near-total disappearance of the fluorescence present inside the contents 101.

During the same observation, the detection device 10 according to the invention is also used to reveal a potential microbial growth inside a container 100 according to a second analysis parameter associated with the presence of turbidity within the container. Indeed, the photodetector 13, equipped with a green filter, is used to monitor the "green" bacterial reaction, which means that it is possible to observe the turbidity present inside the container 100, using said photodetector 13. After an incubation period of the order of 24 hours, an increase in the signal intensity is identifiable in FIG. 8. This increase in the signal intensity, observed thanks to the photodetector 13, indicates the presence of particles within the fluid 101.

As described above and as represented in FIG. 8, system 1 according to the invention makes it possible to connect a detection device 10 to the outside of a container 100, said detection device 10 making it possible to monitor one, or preferably two, analysis criteria or parameters.

As shown in FIG. 8, any event arising inside the container 100 may be monitored continuously. The data obtained during the observation may be stored and compared with the results of other tests of the same type. Furthermore, the various results may be the subject of analyses, in order to confirm preliminary conclusions.

An example of a test performed using the system 1 according to the invention is described in detail below.

Example

Figure 9:
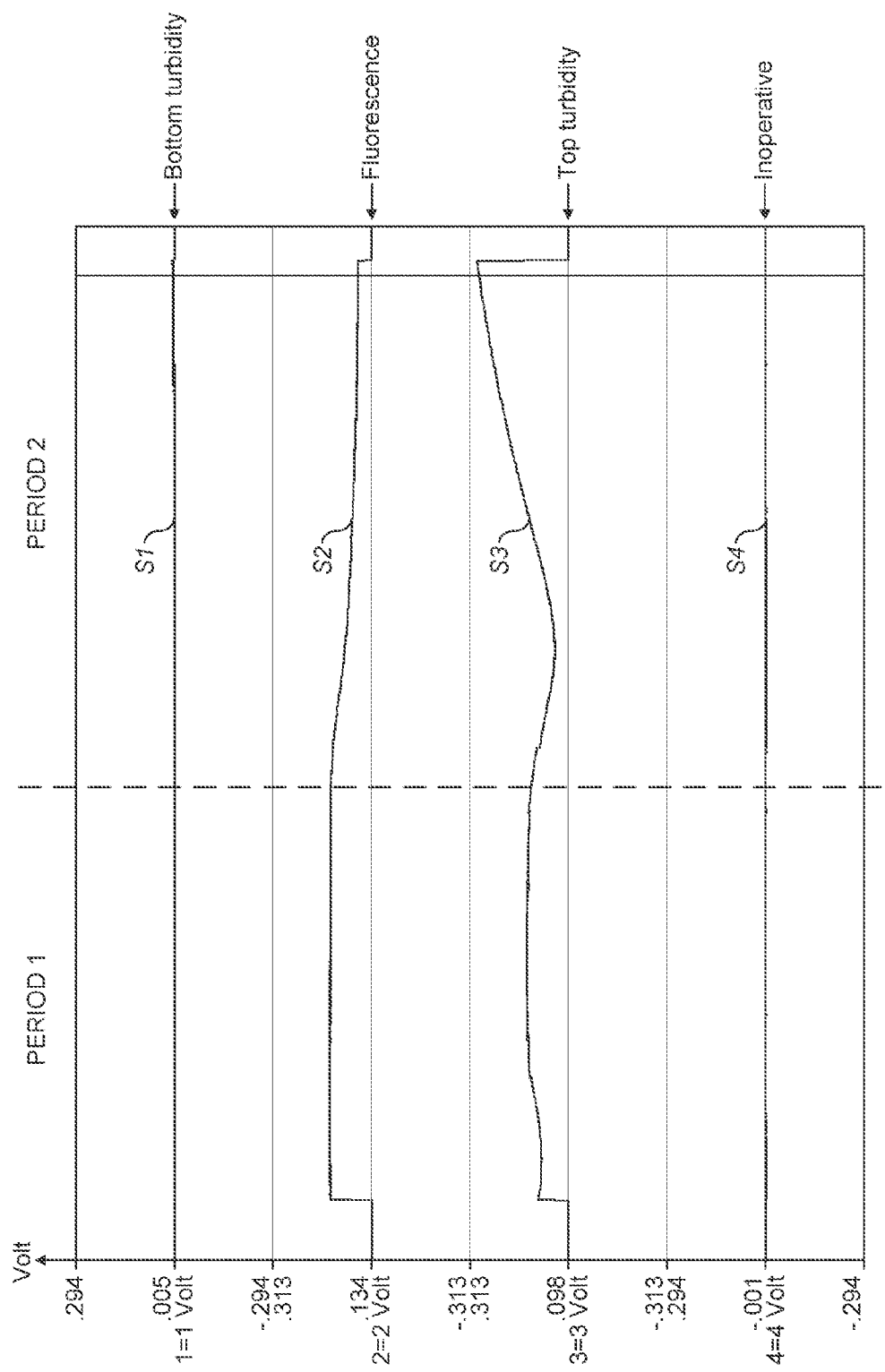
FIG. 9 represents results obtained using a detection system according to an alternative to the embodiment of the invention of FIG. 2, said results comprising notably a first reaction signal concerning a first analysis parameter associated with the presence of turbidity within the container in the bottom position of the container, a second reaction signal concerning the disappearance of fluorescence within the container and a third reaction signal concerning the first analysis parameter associated with the presence of turbidity within the container in the top position of the container.

The results obtained thanks to the test according to the present example are represented in FIG. 9.

Method

"Media Fill Test" culture medium with coloured indicator: "TSB 3P irradiated vegetable peptones with coloured indicator (MFTVCI-D)", reference 51104, bioMérieux, Bioball 550 CPU calibrated strain, *Candida albicans* ATCC 10231, reference 56013, bioMérieux, Rehydration fluid for Bioball, reference 56021, bioMérieux.

A glass tube, filled with 10 ml of culture medium, is inoculated with 55 CPU of *Candida albicans* (100 µl of Bioball bacterial suspension). The tube is fixed to the detection device 10 using an elastic band and placed in a dark room in the horizontal position, similar to the positions shown in FIG. 4, at ambient temperature.

As shown in FIG. 9, four signals S1, S2, S3 and S4 are represented during an observation period comprising a period 1 and a period 2.

Signal S1 is associated with the detection of a potential turbidity within the contents of the container in the bottom position of the container. As shown in FIG. 9, signal S1 is constant throughout the duration of the observation. Thus, the graphic representation of signal indicates that there is no turbidity present within the contents of the container, in the bottom position of said container during periods 1 and 2.

Signal S2 is associated with the detection of a potential fluorescence within the contents of the container. As shown in FIG. 9, signal S2 is constant during period 1, and indicates the presence of a fluorescence within the container. During period 2, signal S2 decreases regularly. Thus, the graphic representation of signal S2 indicates that the fluorescence rate decreases within the container. This disappearing fluorescence indicates that there are microorganisms present within the container.

Signal S3 is associated with the detection of a potential turbidity within the contents of the container in the top position of the container. As shown in FIG. 9, signal S3 is practically constant during period 1. During period 2, signal S3 decreases slightly, and then decreases more steeply, and then finally increases regularly. The different decrease levels are associated with a turbidity measurement within the contents of the container in an observation period, period 2, during which the presence of microorganisms is proven. However, during this period 2, the microorganisms are not homogeneously distributed. Thus, the signal exhibits random variations before stabilising. After a short time, the increase in the number of microorganisms is such that the homogeneous distribution of the microorganisms within the contents of the container makes it possible to obtain a signal S3 which increases regularly over time.

Therefore signal S3 indicates that there is turbidity present within the container. The presence of the turbidity indicates that there are microorganisms present within the container.

Signal S4 is associated with a reference signal corresponding to the detection device 10 being in an inoperative state. This signal S4 makes it possible, notably, to verify the operation of the photodetectors, by comparison of the numerical values of signals S1, S2 and S3 with the numerical value of S4.

Thus, by combining observation of signals S2 and S3, it appears that the presence of microorganisms is confirmed from observation period 2. Depending on the configuration of the control device associated with the detection device, an alarm may be set up to alert the user to the presence of a microbiological contamination within the container.

The invention claimed is:

1. A detection device for detecting the presence of at least one microorganism in the contents of a container comprising a wall with a translucent zone, said detection device comprising:
   a) at least one light source configured to illuminate the contents of the container by emitting an excitation light beam through the translucent zone of the container;
   b) at least one detector positioned at an angle of set value in relation to the direction of the excitation light beam to detect at least one reaction light beam emitted in response to the reaction of the excitation light beam with the contents of the container; and
   c) at least one adjustable connector configured to attach the at least one light source and the at least one detector to an outside wall of the container at a first fixed position and in proximity to the translucent zone and permit movement of the at least one light source and the at least one detector in relation to the translucent zone to one or more other fixed positions on the outside wall of the container,
   wherein the at least one connector is positioned entirely outside of the container.

2. The detection device according to claim 1, wherein said at least one detector comprises at least a first and a second photodetector positioned at a first and a second site in the translucent zone of the container to detect a first and a second reaction light beam and obtain a first and second value of an analysis parameter representative of a potential microbial presence in the contents of the container.

3. The detection device according to claim 2, wherein the first photodetector comprises a red-filtered photodiode and the second photodetector comprises a green-filtered photodiode.

4. The detection device according to claim 1, wherein said at least one detector comprises a first photodetector configured to detect a first reaction light beam and obtain a value n of a first analysis parameter representative of a microbial presence in the contents of the container and a second photodetector configured to detect a second reaction light beam and obtain a value m of a second analysis parameter representative of a microbial presence in the contents of the container.

5. The detection device of claim 4, wherein the first reaction light beam differs from the second reaction light beam.

6. The detection device of claim 1, wherein the at least one light source comprises a light emitting diode.

7. The detection device of claim 1, wherein the at least one detector comprises a photodiode.

8. A detection system comprising:
   a detection device comprising:
   a) at least one light source configured to illuminate the contents of a container by emitting an excitation light beam through a translucent zone of the container;
   b) at least one detector positioned at an angle of set value in relation to the direction of the excitation light beam to detect at least one reaction light beam emitted in response to the reaction of the excitation light beam with the contents of the container;
   c) at least one adjustable connector configured to attach the at least one light source and the at least one detector to an outside wall of the container at a first fixed position and in proximity to the translucent zone and permit movement of the at least one light source and the at least one detector in relation to the translucent zone to one or more other fixed positions on the outside wall of the container; and d) a control device in communication with said at least one light source and said at least one detector, the control device being configured to control the excitation light beam emitted by said at least one light source and control one or more of the processing and analyzing of said at least one reaction light beam, wherein the at least one connector is positioned entirely on the outside of the container.

9. The detection system according to claim 8, wherein the control device further comprises:

a storage medium for storing a first value of a first and second analysis parameter obtained with said at least one detector and a second value of the first and second analysis parameter obtained after a set time period obtained with said at least one detector, the control device being configured to analyze the first and second values of the first and second analysis parameter to determine a potential microbial growth in the contents of the container.

10. The detection system according to claim 8, wherein the control device is configured to continuously receive and store values obtained with said at least one detector.

11. The detection system according to claim 8, wherein the control device comprises an alarm configured to indicate a microbial presence in the contents of the container.

12. A method for detecting the presence of at least one microorganism in a sample, said method comprising:

introducing the sample into a container comprising a wall with at least one translucent zone;

employing a detection system to measure at least one value n of at least one analysis parameter representative of a microbial presence inside the container by:

illuminating the contents of the container through the translucent zone with the light source; and detecting a reaction light beam emitted in response to illuminating the contents with at least one detector configured to obtain said value n of the analysis parameter, wherein the value n increases as the quantity of the at least one microorganism increases in the container;

comparing said value n with a threshold value ns of the same analysis parameter, said threshold value ns indicating the presence of at least one microorganism in the sample; and deducing a contamination of the sample by the at least one microorganism if the value n is equal to or greater than the threshold value ns.

13. The method according to claim 12, wherein the measuring of at least one analysis parameter of the value n comprises measuring the analysis parameter of which decreases as the quantity of said microorganism decreases; and the deducing comprises deducing a contamination of the sample by said at least one microorganism if the value n is less than or equal to the threshold value ns.

14. The method according to claim 13, wherein the value n is associated with a fluorescence of the sample.

15. The method according to claim 12, wherein the measuring of at least a first analysis parameter of a value n1 comprises measuring at least a first analysis parameter of which increases as the quantity of said microorganism increases and measuring at least a second analysis parameter of a value n2 of which decreases as the quantity of said microorganism decreases;

the comparing comprises comparing said value n1 with a threshold value ns1 associated with the first analysis parameter, and comparing said value n2 with a threshold value ns2 associated with the second analysis parameter; and the deducing comprises deducing a contamination of the sample by said at least one microorganism if the value n1 is equal to or greater than the threshold value ns1 and if the value n2 is less than or equal to the threshold value ns2.

16. The method according to claim 12, further comprising contacting the sample with a culture medium.

17. The method according to claim 16, wherein the culture medium is suitable to enable growth of the at least one microorganism.

18. The method according to claim 16, wherein the sample is contacted with the culture medium prior to introduction into the container, after introduction into the container or combinations thereof.

19. The method according to claim 12, further comprising incubating the container at a temperature and for a time period sufficient to grow the at least one microorganism.

20. The method according to claim 12, wherein the value n is associated with a turbidity of the sample.

* * * * *